United States Patent [19]

Seckinger et al.

[11] Patent Number: 5,221,744
[45] Date of Patent: Jun. 22, 1993

[54] ARYLAMINOCARBONYL COMPOUNDS

[75] Inventors: Karl Seckinger, Riegel, Fed. Rep. of Germany; Karlheinz Milzner, Basel, Switzerland; Fred Kuhnen, Weil, Fed. Rep. of Germany; Sasank S. Mohanty, Baden, Switzerland

[73] Assignee: Sandoz Ltd., Basel, Switzerland

[21] Appl. No.: 931,250

[22] Filed: Aug. 17, 1992

Related U.S. Application Data

[63] Continuation of Ser. No. 880,431, May 8, 1992, abandoned.

[30] Foreign Application Priority Data

May 17, 1991 [GB] United Kingdom ............. 9110679

[51] Int. Cl.$^5$ ............... C07D 498/14; C07D 491/12
[52] U.S. Cl. ..................... 504/193; 546/14; 546/22; 546/115; 546/116; 546/83; 544/50; 544/52; 544/92; 544/235; 504/235; 504/225; 504/223; 504/221; 504/247; 504/246; 504/196
[58] Field of Search ............... 546/83, 115, 116, 14, 546/22; 71/92, 94; 544/92, 235, 50, 52

[56] References Cited

U.S. PATENT DOCUMENTS

| H531 | 10/1988 | Ray . | |
|---|---|---|---|
| 4,025,333 | 5/1977 | Golbenk | 71/94 |
| 4,542,244 | 9/1985 | Payne et al. | 71/85 |
| 4,789,394 | 12/1988 | Bohner et al. . | |
| 4,881,967 | 11/1989 | Semple . | |
| 5,024,694 | 6/1991 | Schallner et al. . | |
| 5,039,334 | 8/1991 | Schallner et al. . | |

FOREIGN PATENT DOCUMENTS

| 8287587 | 12/1987 | Australia . |
|---|---|---|
| 104532 | 9/1983 | European Pat. Off. . |
| 230874 | 1/1987 | European Pat. Off. . |
| 60444Y34 | 1/1976 | Japan . |
| 85168518 | 11/1983 | Japan . |
| 86004858 | 5/1984 | Japan . |
| 86078820 | 7/1984 | Japan . |
| 86140810 | 9/1984 | Japan . |
| 89011893 | 5/1987 | Japan . |
| 1503244 | 2/1976 | United Kingdom . |

OTHER PUBLICATIONS

Kim et al. J.O.C. 43(1), 125–31 (1978).

Primary Examiner—Marianne M. Cintins
Assistant Examiner—John Peabody
Attorney, Agent, or Firm—Allen E. Norris

[57] ABSTRACT

Arylaminocarbonyl compounds of the formula (I)

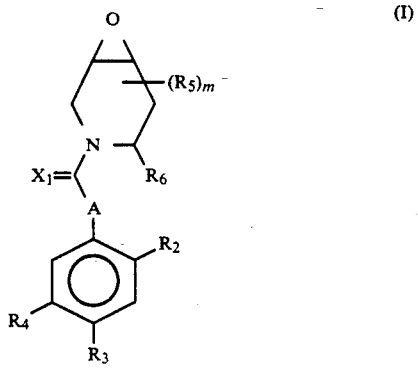

wherein $R_{2-6}$, $X_1$, A and m are as defined in the disclosure, intermediates therefore, synthesis thereof, and the use of said compounds for the control of weeds are described.

10 Claims, No Drawings

ARYLAMINOCARBONYL COMPOUNDS

This is a continuation of application Ser. No. 07/880,431, filed May 8, 1992, now abandoned.

This invention relates to novel arylaminocarbonyl compounds, intermediates therefore, synthesis thereof, and the use of said compounds for the control of weeds.

More particularly, one aspect of this invention relates to a compound of the formula (I)

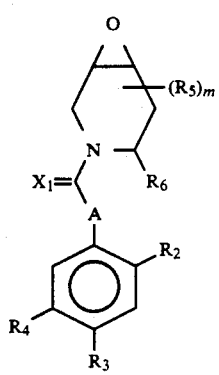

wherein
$R_2$ is halo or hydrogen;
$R_3$ is halo, cyano or $C_{1-4}$alkyl;
$R_4$ is H; halo; $NO_2$; $NH_2$; CN; $C_{1-8}$alkyl optionally substituted by CN; $C_{2-8}$alkenyl optionally substituted by CN; $C_{2-5}$alkinyl; $C_{2-5}$alkoxycarbonyl$C_{1-4}$alkyl, whereby the carbon atom of the alkyl group alpha to the alkoxycarbonyl group may be substituted with one more $C_{2-5}$alkoxycarbonyl groups or a cyano group; $C_{2-5}$alkoxycarbonyl$C_{1-4}$alkoxy$C_{1-4}$alkyl; $C_{2-5}$alkoxycarbonyl$C_{2-5}$alkenyl, whereby the alkenyl group is optionally substituted by halogen; $C_{1-4}$alkylthio$C_{1-4}$alkyl; $C_{1-4}$alkylsulfonyl$C_{1-4}$alkyl; $C_{1-4}$alkylsulfonyl; $C_{1-4}$alkylsulfonyloxy; $C_{1-4}$alkoxy$C_{1-4}$alkoxy; $O(C_{1-4}$alkylene$)_nR_7$; $S(C_{1-4}$alkylene$)_nR_7$; $OCH(SR_8)COOR_9$; $NR_{10}R_{11}$; $COOR_{12}$; $C(O)NR_{13}R_{13}'$; $C(O)R_{14}$; or $R_{15}$;
or $R_3$ and $R_4$ join together with the phenyl ring to form a bicyclic ring containing nine to ten ring atoms, one to three of said ring atoms optionally being selected from oxygen, nitrogen and sulfur, and optionally being substituted with one or more groups selected from $C_{2-8}$alkinyl, halo, oxo, $C_{1-4}$alkylene-$R_{16}$, and $C_{2-8}$alkenyl and $C_{1-8}$alkyl which is itself optionally substituted by $C_{2-5}$alkoxycarbonyl, $C_{1-4}$alkoxy or CN;
$R_5$ is H, $C_{1-4}$alkyl; halogen; OH; $C_{2-4}$alkenyl; or oxo;
$R_6$ is COOH, COOW, COSW, COON=CWW'; CONHSO$_2$W; CONHOCH$_2$COOW; COOCH$_2$OCOW; COOCHWOCOW'; or CONHOCH$_2$COOH;
A is NH;
or A and $R_6$ join together to form —N—C($X_2$)— so oriented such that N is tied to the C($X_1$) moiety of formula (I);
$R_7$ is H; $C_{1-4}$alkyl, $C_{2-5}$alkenyl, $C_{2-5}$alkinyl, or $C_{3-8}$cycloalkyl, which hydrocarbyl is unsubstituted or substituted by one or more halo or by CN; cyclopentanonyl; phenyl optionally substituted by O—$C_{1-4}$alkylene-$COOR_8$; $C_{2-5}$alkanoyl; $C_{2-5}$alkoxycarbonyl wherein the alkoxy is optionally substituted by $C_{1-4}$alkylthio; $C(O)NR_8R_8'$; C(=NOR$_8$)COOR$_8'$; P(O)(OR$_8$)OR$_8'$; $R_{15}$; C(O)$R_{15}$; or cyclopentoxycarbonyl;
$R_8$ and $R_8'$ independently are $C_{1-4}$alkyl;
$R_9$ is $C_{1-4}$alkyl optionally substituted by one or more halo;
$R_{10}$ is H or $C_{1-4}$alkyl;
$R_{11}$ is H; $C_{1-4}$alkyl, optionally substituted by P(O)(OR$_8$)$R_8'$; $C_{2-5}$alkanoyl; $C_{2-5}$alkoxycarbonyl; or $C_{2-5}$alkoxycarbonyl$C_{1-4}$-alkyl;
$R_{12}$ is N=$C_{2-8}$alkylidene; or $C_{1-4}$alkyl optionally substituted by one or more groups selected from halo, $C_{1-4}$alkoxy, CN, tri($C_{1-4}$alkyl)silyloxy, tri($C_{1-4}$alkyl)silyl, $C_{2-5}$alkoxycarbonyl, P(O)(OR$_8$)OR$_8'$, $C_{2-5}$alkanoyloxy, and di($C_{1-4}$alkyl)aminocarbonyloxy in which both alkyl groups may be tied together to form a saturated 5 to 6 membered heteroring optionally containing one further heteroatom selected from O, S and N, and in which any further N-heteroatom present may, depending on the hydrogenation degree of the heteroring, bear a hydrogen or a $C_{1-4}$alkyl group;
$R_{13}$ is H or $C_{1-4}$alkyl; and
$R_{13}'$ is H, $C_{1-4}$alkyl optionally substituted by halo, $C_{1-4}$alkoxy, phenyl, CHO, $C_{2-5}$alkanoyl, $C_{1-4}$alkylsulfonyl, $C_{2-5}$alkoxycarbonyl$C_{1-4}$alkyl or $C_{2-5}$alkoxycarbonyl$C_{1-4}$alkoxy;
or $R_{13}$ and $R_{13}'$ together form a 4 to 6 membered heteroring optionally containing one or two further heteroatoms selected from O, S and N, whereby, depending on the hydrogenation degree of the heteroring, any further N-heteroatom may bear hydrogen or be substituted by $C_{1-4}$alkyl;
$R_{14}$ is H or $C_{1-4}$alkyl;
$R_{15}$ is a heterocyclic ring having 5 or 6 ring atoms, one to three of said ring atom being selected from oxygen, sulfur and nitrogen, which ring is optionally substituted with one or more groups selected from $C_{1-4}$alkyl and $C_{2-5}$alkoxycarbonyl;
$R_{16}$ is tetrahydropyranyl, 5,6-dihydro-2H-thiinyl, pyridyl, pyrazinyl, oxazolyl, or oxadiazolyl all of which are optionally substituted with $C_{1-4}$alkyl;
W and W' are independently $C_{1-8}$alkyl, $C_{2-8}$alkenyl, $C_{2-8}$alkinyl, or phenyl, each of which is optionally substituted by CN, $C_{1-4}$alkoxy or one or more halo;
$X_1$ and $X_2$ are independently O or S;
n is 0 or 1; and
m is 0 to 2.

Compounds of the formula (I) wherein A and $R_6$ join together are hereinafter referred to as hydantoins. Compounds of the formula (I) wherein A and $R_6$ do not join together are hereinafter referred to as ureas.

Any alkyl group in the compound of formula (I) may be branched or straight chain and preferably has one to four backbone carbon atoms.

Any alkenyl or alkinyl group may be either branched or straight chain and preferably has three to five backbone carbon atoms.

Any cycloalkenyl group preferably has five to six carbon ring atoms.

Any cycloalkyl group preferably has three to five carbon ring atoms.

Halo as used herein refers to fluoro, chloro, bromo and iodo, and unless otherwise noted preferably will be fluoro or chloro.

Where $R_3$ and $R_4$ join together with the phenyl ring to form a bicyclic ring, it is preferably an indanone; a benzazinone, particularly a quinolinone; a benzoxazinone; a benzodiazinone, particularly dihydroquinoxalinone; a benzothiazinone; a benzodioxane; a benzopyrane; a benzopyrone, particularly coumarin; a benzazole, particularly an indole, an indolone, an indazole, a benzotriazole, an isatine or a benzimidazolone; a benzoxazolone; a benzothiazolone; a benzofurane; or a benzdioxolane.

Where $R_5$ is halogen, it is preferably chlorine or fluorine, more preferably fluorine.

Where m is 2, each $R_5$ substituent may be the same or different.

$R_2$ is preferably chlorine or fluorine, more preferably fluorine.

$R_3$ is preferably bromine, chlorine, fluorine, methyl or cyano.

$R_4$ is preferably $COOR_{12}$, $OR_7$ or $CONR_{13}R_{13}'$; or $R_3$ and $R_4$ preferably join together to form a benzoxazinone optionally substituted by $C_{2-8}$alkinyl.

$R_5$ is preferably hydrogen or fluorine.

$R_6$ is preferably joins together with A to form —N—C(O)—.

$R_7$ is preferably $C_{1-4}$alkyl, $C_{2-5}$alkenyl or $C_{2-5}$alkinyl.

$R_{12}$ is preferably $C_{1-4}$alkyl optionally substituted by halo or CN.

$R_{13}$ is preferably H.

$R_{13}'$ is preferably $C_{1-4}$alkyl optionally substituted by halo.

$X_1$ and $X_2$ are preferably O.

Urea compounds of the formula (I) may be prepared by reacting a compound of the formula (II)

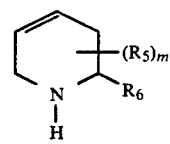

(II)

wherein $R_{2-4}$ and $X_1$ are as previously defined, with a compound of the formula (III)

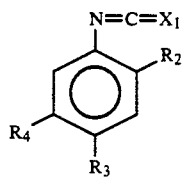

(III)

wherein $R_{5-6}$ and m are as previously defined.

This reaction may be carried out in an inert solvent such as toluene, diethylether or methylene chloride at a temperature ranging from 0°–100° C., preferably at or near ambient temperature. The desired end-product is isolated and purified according to known techniques, for example, by evaporation of solvent, chromatography and extraction.

Compounds of the formula (II) are either known or can be prepared from known compounds following procedures analogous to those known in the art.

Compounds of the formula (III) are believed to be novel and form a further aspect of the invention of this application. Compounds of the formula III may be prepared by reacting a compound of the formula (IV)

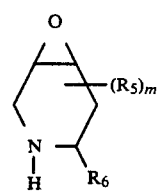

(IV)

wherein $R_5$, $R_6$ and m are as previously defined, with an epoxide forming agent. Suitable such epoxide forming agents include those known to those skilled in the art, e.g., $H_2O_2$, $t\text{-}BuO_2H$, NBS, $NaBO_3$, aliphatic or aromatic peroxyacids such as peroxyacetic acid and peroxytrifluoracetic acid or e.g. m-chloroperbenzoic acid. This epoxidation reaction may be carried out under conditions known in the art.

Compounds of the formulae (IV) are either known or can be prepared from known compounds following procedures analogous to those known in the art.

Hydantoin compounds of the formula (I) may be prepared by reacting the compound of formula (V)

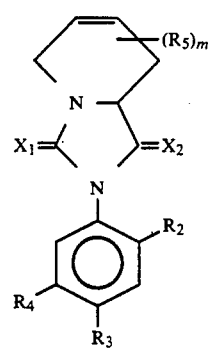

(V)

wherein $R_{2-5}$, $X_1$, $X_2$ and m are as previously defined, with an epoxide forming agent, as previously described, under conditions typical for epoxidation reactions, as previously described.

Compounds of the formula (V) may be prepared by reacting a compound of the formula (II) hereinabove defined with a compound of the formula (IVa)

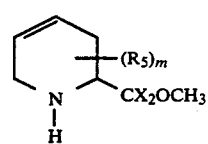

(IVa)

wherein $X_2$, $R_5$ and m are as previously defined.

This condensation reaction is preferably carried out in an inert solvent such as toluene. Condensation is facilitated by the presence of a nucleophilic agent such as a tertiary amine, e.g., a tri(alkyl)amine such as tri(ethyl)amine. Suitable reaction temperatures range from room to reflux temperature, and preferably is at or near ambient temperature. The desired end-product is isolated and purified according to known techniques, for example, by evaporation of solvent, filtration and crystallization.

Compounds of the formulae (IVa) are known or can be prepared from known compounds following procedures analogous known procedures.

The compounds of formula (I) are effective in controlling the growth of plants. By plants it is meant germinating seeds, merging seedlings and established vegetation including underground portions. In particular, the compounds are useful as herbicides as indicated by causing damage to both monocotyledoneous and dicotyledoneous plants in various standard evaluations for determining such effects. The herbicidal effects are exhibited both pre- and post-emergence the plants. Such herbicidal effects indicate that the compounds of formula (I) are particularly of interest in combatting weeds (unwanted plants).

The compounds of the formula (I) are indicated mainly to be stronger acting against dicotyledoneous plants than monocotyledoneous plants. Relatively less toxicity towards crops than towards weeds is further indicated. Hence, the compounds are of particular interest as selective herbicides to combat weeds in a crop locus, particularly as locus of a crop such as, for example, sugarbeet, sunflower, cotton soybean, corn and wheat.

The present invention therefore also provides a method of combatting weeds in a locus which comprises applying to the weeds or their locus a herbicidally effective amount of a compound of the invention. When selective action is desired in crop locus, the amount applied will be sufficient to combat weeds without substantially damaging the crop.

For general herbicidal as well as selective herbicidal use of the compounds of the invention, the particular amounts to be applied will vary depending upon recognized factors such as the compound employed, the plants primarily in the locus, the timing, mode and formulation in application, the various conditions of treatment such as soil and weather and the like. However, in general, satisfactory results in weed control are usually obtained upon application of the compounds of the invention at a rate in the range of from 0.01 to 5 kg/hectare, more usually 0.02 to 1 kg/hectare, and preferably 0.02 to 0.5 kg/hectare, the application being repeated as necessary. When used in crops, the application usually will not exceed about 1 kg/hectare, and is usually in the range of 0.01 to 0.5 kg/hectare.

For practical use as herbicides, the compounds of formula (I) may be and are preferably employed in herbicidal compositions comprising a herbicidal effective amount of the compound and an inert carier which is agriculturally acceptable in the sense of not, by reason of its presence, poisoning the agricultural environment including the immediate soil of application or any crops present therein or otherwise being unsafe for application. Such compositions of formulations may contain 0.01% to 99% by weight of active ingredient, from 0 to 20% by weight of agriculturally acceptable surfactants and 1 to 99.99% by weight of the inert carrier. Higher ratios of surfactant to active ingredient are sometimes desirable and are achieved by incorporation into the formulation or by tank mixing. Application forms of composition typically contain between 0.01 and 25% by weight of active ingredient, but lower or higher levels of active ingredient can, of course, be present depending on the intended use and the physical properties of the compound. Concentrate forms of composition intended to be diluted before use generally contain between 2 and 90%, preferably between 10 and 80% by weight of active ingredient.

Useful compositions or formulations of the compounds of the invention include dusts, granules, pellets, suspension concentrates, wettable powders, emulsifiable concentrates and the like. They are obtained by conventional manner, e.g. by mixing the compounds of the invention with the inert carrier. More specifically, liquid compositions are obtained by mixing the ingredients, fine solid compositions by blending and, usually grinding, suspensions by wet milling and granules and pellets by impregnating or coating (preformed) granular carriers with the active ingredient or by agglomeration techniques.

For example, dusts can be prepared by grinding and blending the active compound with a solid inert carrier such as talc, clay, silica and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

Alternatively, the compounds of the invention may be used in micro-encapsulated form.

Agriculturally acceptable additives may be employed in the herbicidal compositions to improve the performance of the active ingredient and to reduce foaming, caking and corrosion.

Surfactant as used herein means agriculturally acceptable material which imparts emulsifiability, spreading, wetting, dispersibility or other surface-modifying properties properties. Examples of surfactants are sodium lignin sulphonate and lauryl sulphate.

Carriers as used herein mean a liquid or solid material used to dilute a concentrated material to a usable or desirable strength. For dusts or granules it can be e.g. talc, kaolin or diatomaeous earth, for liquid concentrate forms, a hydrocarbon such as xylene or an alcohol such as isopropanol; and for liquid application forms, e.g. water or diesel oil.

The compositions of this application can also comprise other compounds having biological activity, e.g. compounds having similar or complementary herbicidal activity or compounds having antidotal, fungicidal or insecticidal activity.

Typical herbicidal composition, according to this invention, are illustrated by the following Examples A, B and C in which the quantities are in parts by weight.

EXAMPLE A

Preparation of a Dust

10 Parts of a compound of formula (I) and 90 parts of powdered talc are mixed in a mechanical grinder-blender and are ground until a homogeneous, free-flowing dust of the desired particle size is obtained. This dust is suitable for direct application to the site of the weed infestation.

EXAMPLE B

Preparation of Wettable Powder

25 Parts of a compound of formula (I) are mixed and milled with 25 parts of synthetic fine silica, 2 parts of sodium lauryl sulphate, 3 parts of sodium ligninsulphonate and 45 parts of finely divided kaolin until the mean particle size is about 5 micron. The resulting wettable powder is diluted with water before use to a spray liquor with the desired concentration.

EXAMPLE C

Preparation of Emulsifiable Concentrate (EC)

13.37 Parts of a compound of formula (I) are mixed in a beaker with 1.43 parts of Toximul 360A (a mixture of anionic and non-ionic surfactants containing largely anionic surfactants), 5.61 parts of Toximul 360A (a mixture of anionic and non-ionic surfactants containing largely non-ionic surfactants), 23.79 parts of dimethylformamide and 55.8 parts of Tenneco 500–100 (predominantly a mixture of alkylated aromatics such as xylene and ethylbenzene) until solution is effected. The resulting EC is diluted with water for use.

FINAL COMPOUNDS

Unless otherwise indicated, temperatures herein stated are in Celsius.

EXAMPLE 1

1-[[(4-chloro-2-fluoro-5-isopropoxyphenyl)amino]carbonyl-4,5-epoxy-2-piperidinecarboxylic acid-methyl ester To a stirred solution of 0.91 g (0.0058 mol) of 4,5-epoxy-2-piperidinecarboxylic acid-methyl ester in 30 ml of dry toluene are added dropwise without cooling 1.33 g (0.0058 mol) of 4-chloro-2-fluoro-5-isopropoxy-phenyl isocyanate, dissolved in 50 ml of dry toluene.

When the addition is complete the reaction solution is stirred an additional four hours at room temperature and is then evaporated to dryness.

The residual syrup is chromatographed on a silica gel column.

Elution with diethyl ether-hexane 1:1 affords the title compound as a yellowish viscous oil. Rf=0.51 on silica gel with ethyl acetate-hexane 1:1 (Compound 1.2, Table A).

Analogous to the procedure set forth in Example A, the compounds of Table 1 are obtained.

EXAMPLE 2

2-chloro-4-fluoro-5-(hexahydro-1,3-dioxo imidazo[1,5a]6,7-epoxy-pyridin-2(3H)-yl-benzoic acid-1-methylethylester To the well stirred mixture of 2.75 g (0.0057 mol) of 2-chloro-4-fluoro-5-(4,5,8,8a-tetrahydro-1,3-dioxoimidazo-[1,5a]pyridine-2(3H)-yl)-benzoic acid-1-methylethylester, 1.3 g (0.015 mol) of $NaHCO_3$ and 50 ml of methylene chloride ($CH_2Cl_2$) is added dropwise, without cooling, the dried ($Na_2SO_4$) solution of 1.65 g of m-chloroperbenzoic acid (80%; 0.0076 mol) in 50 ml of dry $CH_2Cl_2$.

After being kept at ambient temperature for three days, the reaction mixture is washed with 100 ml of water which contains 1.5 g of $NaHSO_3$.

Then the organic layer is separated, washed with water (100 ml), dried ($Na_2SO_4$) and evaporated in vacuo.

The residue is chromatographed on a silica gel column.

Elution with diethyl ether-hexane 1:1 affords the title compound as a white amorphous solid, which is homogeneous by TLC. Rf=0,28 on silica gel with ethyl acetate-hexane 1:1 (Ex. No. 2.83, Table 2).

Following procedures analogous to Example B, the compounds of Table 2 are obtained.

TABLE 1

Compounds of the Formula I wherein A is NH and $X_1$ is O

PART A

| Example | $R_2$ | $R_3$ | $R_4$ | $R_6$ | $(R_5)m$ | m.p. or Rf on silica gel |
|---|---|---|---|---|---|---|
| 1.1 | F | Cl | $OC_3H_{7-i}$ | COOH | H | |
| 1.2 | F | Cl | $OC_3H_{7-i}$ | $COOCH_3$ | H | 0.51; ethylacetate:hexane 1:1 |
| 1.3 | F | Cl | $OCOOCH_3$ | $COOCH_3$ | H | |
| 1.4 | F | Cl | $OSO_2CH_3$ | $COOCH_3$ | H | |
| 1.5 | Cl | Cl | $OC_3H_{7-i}$ | $COOCH_3$ | H | |
| 1.6 | H | Cl | H | COOH | H | |
| 1.7 | F | Cl | Br | $COOCH_3$ | H | |
| 1.8 | F | Cl | I | " | H | |
| 1.9 | F | Cl | Cl | " | H | |
| 1.10 | F | Cl | CN | " | H | |
| 1.11 | F | Cl | $OCH_2C\equiv CH$ | " | H | |
| 1.12 | F | Cl | $OC_3H_{7-n}$ | " | H | |
| 1.13 | F | Cl | $OCH_2CH_3$ | " | H | |
| 1.14 | F | Cl | $OCH_3$ | " | H | |
| 1.15 | F | Cl | O-cyclopentyl | " | H | |
| 1.16 | F | Cl | $OCH_2CH=CHCH_3$ | " | H | |
| 1.17 | F | Cl | $OCH_2C(CH_3)=CH_2$ | $COOCH_3$ | H | |
| 1.18 | F | Cl | $OCH(CH_3)CH=CH_2$ | " | H | |
| 1.19 | F | Cl | $OCH_2CH=C(CH_3)_2$ | " | H | |
| 1.20 | F | Cl | $OCH_2C(Br)=CH_2$ | " | H | |
| 1.21 | F | Cl | $OCH_2CH=CH-Br$ | " | H | |
| 1.22 | F | Cl | $OCH_2CH=CH-COOCH_3$ | " | H | |
| 1.23 | F | Cl | $OC_3H_{7-i}$ | $COOC_3H_{7-i}$ | H | |
| 1.24 | F | Cl | " | $COOCH_2CH=CH_2$ | H | |
| 1.25 | F | Cl | " | $COOCH_2C\equiv CH$ | H | |
| 1.26 | F | Cl | " | $COOC(CH_3)HOCOCH_3$ | H | |
| 1.27 | F | Cl | " | $COOCH_2OCOCH_3$ | H | |
| 1.28 | F | Cl | " | $COON=C(CH_3)_2$ | H | |
| 1.29 | F | Cl | " | $CONHOCH_2COOCH_3$ | " | |
| 1.30 | F | Cl | " | $CONHSO_2$-phenyl | " | |
| 1.31 | F | Cl | " | $COSCH_2CH_3$ | " | |
| 1.32 | F | $CH_3$ | " | $COOCH_3$ | " | |
| 1.33 | F | CN | " | " | " | |
| 1.34 | F | CN | $COOC_4H_{9-s}$ | " | " | |
| 1.35 | F | Cl | $CH_2SCH_3$ | " | " | |
| 1.36 | F | Cl | $CH_2SO_2CH_3$ | " | " | |

TABLE 1-continued

| | | | | | |
|---|---|---|---|---|---|
| 1.37 | F | Cl | SO$_2$C$_3$H$_{7\text{-}i}$ | " | " |
| 1.38 | F | Cl | OC$_3$H$_{7\text{-}i}$ | " | 8-OH |
| 1.39 | F | Cl | OC$_3$H$_{7\text{-}i}$ | COOCH$_2$OCH$_2$CH$_2$OCH$_3$ | " |
| 1.40 | F | Cl | OC$_3$H$_{7\text{-}i}$ | COOCH$_3$ | 2-CH$_3$ |
| 1.41 | F | Cl | " | " | 6-CH$_3$ |
| 1.42 | F | Cl | " | " | 4(5)-CH$_3$[1] |
| 1.43 | F | Cl | " | " | 4(5)-CH$_2$CH$_3$[1] |
| 1.44 | F | Cl | " | " | 4(5)Cl[1] |
| 1.45 | F | Cl | " | " | 8-F |
| 1.46 | F | Cl | " | " | 3,6-(CH$_3$)$_2$ |
| 1.47 | F | Cl | " | " | 4,6,6-(CH$_3$)$_3$ |
| 1.48 | F | Cl | OC(CH$_3$)C≡CH | COOCH$_3$ | H |
| 1.49 | F | Cl | OCH(CH$_3$)CH$_2$CH$_3$ | COOCH$_3$ | H |
| 1.50 | F | Cl | OCH$_2$-phenyl | " | H |
| 1.51 | F | Cl | OCH(CH$_3$)phenyl | " | H |
| 1.52 | F | Cl | OCH(CH$_3$)CH$_2$OCH$_3$ | " | H |
| 1.53 | F | Cl | OCH$_2$C(O)CH$_3$ | " | H |
| 1.54 | F | Cl | OCH$_2$CH=CH$_2$ | " | H |
| 1.55 | F | Cl | OCH$_2$CH=CHCl | " | H |
| 1.56 | F | Cl | OCH$_2$CH(Cl)=CH$_2$ | " | H |
| 1.57 | F | Cl | OCH$_2$-(2,2-di-Cl-cyclopropyl) | " | H |
| 1.58 | F | Cl | OCH$_2$(2-Cl-cyclopropyl) | " | H |
| 1.59 | F | Cl | OCH$_2$-cyclopropyl | COOCH$_3$ | H |
| 1.60 | F | Cl | OCH$_2$CH$_2$OCH$_2$CH$_3$ | " | H |
| 1.61 | F | Cl | OCH$_2$-(tetrahydrofuran-2-yl) | " | H |
| 1.62 | F | Cl | OCH$_2$-(tetrahydropyran-2-yl) | " | H |
| 1.63 | F | Cl | OCH$_2$-(5,6-dihydro-2-H-thiin-3-yl) | " | H |
| 1.64 | F | Cl | OCH$_2$—C(=NOCH$_3$)COOC$_2$H$_5$ | " | H |
| 1.65 | F | Cl | OCH$_2$-(1,3-dioxolan-2-yl) | " | H |
| 1.66 | F | Cl | OCH$_2$-(1,3-dithiolan-2-yl) | " | H |
| 1.67 | F | Cl | OCH$_2$—CO—(1,4-oxazin-4-yl) | " | H |
| 1.68 | F | Cl | OCH$_2$COOC$_5$H$_{11\text{-}n}$ | " | H |
| 1.69 | F | Cl | O-(2-oxo-cyclopentyl-1) | " | H |
| 1.70 | F | Cl | OP(O)(OCH$_3$)$_2$ | COOCH$_3$ | H |
| 1.71 | F | Cl | OCH(SCH$_3$)—COOCH$_2$CH$_2$Cl | " | H |
| 1.72 | F | Cl | OCH$_2$P(O)(OCH$_2$CH$_3$)$_2$ | " | H |
| 1.73 | F | Cl | OCH$_2$CF$_3$ | " | H |
| 1.74 | F | Cl | OCHF$_2$ | " | H |
| 1.75 | F | Cl | OCH$_2$COOcyclopentyl | " | H |
| 1.76 | F | Cl | OCH$_2$-(1-pyrazolyl) | " | H |
| 1.77 | F | Cl | 4-[C$_2$H$_5$OOC—CH(CH$_3$)—O]phenoxy | " | H |
| 1.78 | F | Cl | OCH$_2$-(thein-2-yl) | " | H |
| 1.79 | F | Cl | OCH(CH$_3$)-(3-CH$_3$-1,2,4-oxadiazol-5-yl) | " | H |
| 1.80 | F | Cl | SC$_3$H$_{7\text{-}i}$ | " | H |
| 1.81 | F | Cl | SCH$_2$C≡CH | COOCH$_3$ | H |
| 1.82 | F | Cl | SCH$_2$COOC$_2$H$_5$ | " | H |
| 1.83 | F | Cl | SCH(CH$_3$)—COOC$_2$H$_5$ | " | H |
| 1.84 | F | Cl | SCH$_2$-phenyl | " | H |
| 1.85 | F | Cl | S-(tetrahydro-pyran-2-yl) | " | H |
| 1.86 | F | Cl | NCH$_2$COOC$_2$H$_5$ | " | H |
| 1.87 | F | Cl | N(CH$_3$)$_2$ | " | H |
| 1.88 | F | Cl | N—(CH$_3$)—COOCH$_2$CH$_3$ | " | H |
| 1.89 | F | Cl | NHCOCH(CH$_3$)—CH$_2$CH$_3$ | " | H |
| 1.90 | F | Cl | NHCH(C$_2$H$_5$)—P(O)(C$_2$H$_5$)(OC$_2$H$_5$) | " | H |
| 1.91 | F | Cl | COOC$_3$H$_{7\text{-}i}$ | " | H |
| 1.92 | F | Cl | COOCH(CH$_2$F)$_2$ | " | H |
| 1.93 | F | Cl | COOCH$_2$CH$_2$OCH$_3$ | " | H |
| 1.94 | F | Cl | COON=C(CH$_3$)$_2$ | " | H |
| 1.95 | F | Cl | COOCH$_2$F | " | H |
| 1.96 | F | Cl | COOCH$_2$CH$_2$OSi(CH$_3$)$_3$ | COOCH$_3$ | H |
| 1.97 | F | Cl | COOCH$_2$Si(CH$_3$)$_3$ | " | H |
| 1.98 | F | Cl | COOCH$_2$CH$_2$P(O)(OCH$_3$)$_2$ | " | H |
| 1.99 | F | Cl | COOCH(CH$_3$)CH$_2$Si(CH$_3$)$_3$ | " | H |
| 1.100 | F | Cl | COOCH(C$_2$H$_5$)P(O)(OCH$_3$)$_2$ | " | H |
| 1.101 | F | Cl | COOCH$_2$COOC$_2$H$_5$ | " | H |
| 1.102 | F | Cl | COOCH$_2$OCOCH$_3$ | " | H |
| 1.103 | F | Cl | COOCH(CH$_3$)OCO-piperidin-1-yl | " | H |
| 1.104 | F | Cl | CON(CH$_3$)$_2$ | " | H |
| 1.105 | F | Cl | CON(CH$_3$)OCH$_3$ | " | H |
| 1.106 | F | Cl | CONHSO$_2$CH$_3$ | " | H |
| 1.107 | F | Cl | CONHOCH$_2$COOC$_2$H$_5$ | " | H |
| 1.108 | F | Cl | CONHCH$_2$COOC$_2$H$_5$ | COOCH$_3$ | H |
| 1.109 | F | Cl | CHO | " | H |
| 1.110 | F | Cl | COOCH$_3$ | " | H |
| 1.111 | F | Cl | 4-(C$_2$H$_5$OOC)-1,3-dioxolan-2-yl | " | H |
| 1.112 | F | Cl | 2-CH$_3$-1,3-dioxolan-2-yl | " | H |
| 1.113 | F | Cl | 4,4-di-CH$_3$-(4,5-dihydrooxazol-2-yl) | " | H |
| 1.114 | F | Cl | CH$_2$CH(CH$_3$)$_2$ | " | H |
| 1.116 | F | Cl | CH$_2$COOC$_2$H$_5$ | " | H |
| 1.117 | F | Cl | CH$_2$C(CN)(CH$_3$)—COOC$_2$H$_5$ | " | H |
| 1.118 | F | Cl | CH$_2$C—(CH$_3$)(COOC$_2$H$_5$)$_2$ | " | H |
| 1.119 | F | Cl | CH$_2$OCH$_3$ | " | H |

TABLE 1-continued

| | | | | | |
|---|---|---|---|---|---|
| 1.120 | F | Cl | CH$_2$OCH$_2$COOC$_2$H$_5$ | " | H |
| 1.121 | F | Cl | CH$_2$NHCH$_2$COOC$_2$H$_5$ | COOCH$_3$ | H |
| 1.122 | F | Cl | CH$_2$CH$_2$CN | " | H |
| 1.123 | F | Cl | CH$_2$CH$_2$COOC$_2$H$_5$ | " | H |
| 1.124 | F | Cl | CH$_2$CH(CH$_3$)—COOC$_2$H$_5$ | " | H |
| 1.125 | F | Cl | CH=CH—CN | " | H |
| 1.126 | F | Cl | CH=CH—COOC$_2$H$_5$ | " | H |
| 1.127 | F | Cl | CH=C(Br)—COOC$_2$H$_5$ | " | H |

Part B: Compounds of the formula I wherein A is NH, X$_1$ is O, m is 0 and the moiety 2-R$_2$-4-R$_3$-5-R$_4$-phenyl is represented below as Ar.

| Ex. No. | Ar | R$_6$ | m.p. or Rf on silica gel |
|---|---|---|---|
| 1.128 | 5-F-indan-1-on-6-yl | COOCH$_3$ | |
| 1.129 | 4-(C$_2$H$_5$OCOCH$_2$)-7-F-Ar$_1$[3] | " | |
| 1.130 | (CH$_3$OCH$_2$)-7-F—Ar$_1$ | " | |
| 1.131 | 4-(CNCH$_2$)-7-F—Ar$_1$ | " | |
| 1.132 | 4-CH$_3$-7-F—Ar$_1$ | " | |
| 1.133 | 4-allyl-7-F—Ar$_1$ | " | |
| 1.134 | 4-CH$_2$-(tetrahydropyran-4-yl)-7-F—Ar$_1$ | " | |
| 1.135 | 4-CH$_2$-(5,6-dihydro-2H-thiin-3-yl)-7-F—Ar$_1$ | " | |
| 1.137 | 4-CH$_2$-(2-pyrazinyl)-7-F—Ar$_1$ | " | |
| 1.138 | 2,2,5-tri-F-benzo[d]-dioxole-6-yl | COOCH$_3$ | |
| 1.139 | 4-CH$_3$-7-F-benzo[e]-1,3-dioxine-6-yl | " | |
| 1.140 | 4-(2-propynyl)-7-F-benzo[b]-1,4-thiazin-3-on-6-yl | " | |
| 1.141 | 4-(2-propynyl)-7-F—Ar$_1$ | " | |
| 1.142 | 1-(2-propynyl)-6-F—Ar$_2$[4] | " | |
| 1.143 | 1-allyl-6-F—Ar$_2$ | " | |
| 1.144 | 1-(2-propynyl)-6-F—Ar$_3$[5] | " | |
| 1.145 | 1-allyl-6-F—Ar$_3$ | " | |
| 1.146 | 1-allyl-6-F-quinoline-2(1H)-on-7-yl | " | |
| 1.147 | 3-(2-propynyl)-6-F-benzo[d]-1,3-oxazole-2(3H)-on-5-yl | " | |
| 1.148 | 4-(1,2-oxazole-3-yl-CH$_2$)-7-F—Ar$_1$ | " | |
| 1.149 | 4-(5-CH$_3$-1,2,4-oxadiazol-3-yl-CH$_2$)-7-F—Ar$_1$ | COOCH$_3$ | |
| 1.150 | 3-(1,2-oxazole-3-yl-CH$_2$)-6-F—Ar$_4$[6] | " | |
| 1.151 | 3-(2-pyridyl-CH$_2$)-6-F—Ar$_4$ | " | |
| 1.152 | 5-F-2,3-dihydro-benzo[b]furan-6-yl | " | |
| 1.153 | 5-F-1-CH$_3$-indol-6-yl | " | |
| 1.154 | 1-(2-propynyl)-5-F-benzo[d]pyrazol-6-yl | " | |
| 1.155 | 1-(2-propynyl)-5-F-benzo[d]-1,2,3-triazol-6-yl | " | |
| 1.156 | 1-allyl-5-F-1,3-dihydro-indol-2-on-6-yl | " | |
| 1.157 | 5-F-1,3-dimethyl-1,3-dihydro-indol-2-on-6-yl | " | |
| 1.158 | 5-F-benzo[d]imidazol-2(1H, 3H)-on-6-yl | " | |
| 1.159 | 5-F-1-(2-propynyl)-1H-indol-2,3-dion-6-yl | " | |
| 1.160 | 6-F-chroman-7-yl | COOCH$_3$ | |
| 1.161 | 6-F-2,3-dihydrobenzo[b]-1,4-dioxin-7-yl | " | |
| 1.162 | 6-F-1-(2-propynyl)-3,4-dihydroquinolin-2(1H)-on-7-yl | " | |
| 1.163 | 7-F-4-isopropyl-chromen-2-on-6-yl | COOCH$_3$ | |

TABLE 2

Compounds of the formula I wherein A and R$_6$ join together to form —N(CX$_2$) - so oriented such that N is tied to the C(X$_1$) moiety of formula I Part A

| Ex. No. | R$_2$ | R$_3$ | R$_4$ | X$_1$ | X$_2$ | (R$_5$)$_m$ | m.p. or Rf on silical gel |
|---|---|---|---|---|---|---|---|
| 2.1 | Cl | Cl | OC$_3$H$_7$-i | O | O | H | |
| 2.2 | F | Cl | OH | O | O | H | |
| 2.3 | F | Cl | OC$_3$H$_7$-i | O | O | H | 100–102° |
| 2.4 | F | Cl | OC$_3$H$_7$-i | S | O | H | |
| 2.5 | F | Cl | OCH$_3$ | O | O | H | 141–142° |
| 2.6 | F | Cl | OCH$_2$CN | O | O | H | |
| 2.7 | F | Cl | OCH(CH$_3$)—C≡CH | O | O | H | 121–123° |
| 2.8 | F | Cl | OC$_3$H$_7$-i | S | S | H | |
| 2.9 | F | Cl | I | O | O | H | |
| 2.10 | F | Cl | Cl | O | O | H | |
| 2.11 | F | Cl | CN | O | O | H | |

| Ex. No. | R$_2$ | R$_3$ | R$_4$ | X$_1$ = X$_2$ | (R$_5$)$_m$ | m.p. or Rf on silica gel |
|---|---|---|---|---|---|---|
| 2.12 | F | Cl | OSO$_2$CH$_3$ | O | H | |
| 2.13 | F | Cl | OCH$_2$C≡CH | O | H | |
| 2.14 | F | Cl | OC$_3$H$_7$-n | O | H | |
| 2.15 | F | Cl | OCH$_2$CHd$_3$ | O | H | |
| 2.16 | F | Cl | O-cyclopentyl | O | H | |
| 2.17 | F | Cl | OCOOCH$_3$ | O | H | |
| 2.18 | F | Cl | OCH$_2$CH≡CHCH$_3$ | O | H | |
| 2.19 | F | Cl | OCH(CH$_3$)CH≡CH$_2$ | O | H | |
| 2.20 | F | Cl | OCH$_2$C(CH$_3$)≡CH$_2$ | O | H | |
| 2.21 | F | Cl | COOC$_3$H$_7$-i | O | oxo | |

TABLE 2-continued

| | | | | | | |
|---|---|---|---|---|---|---|
| 2.22 | F | Cl | OCH$_2$C(Br)≡CH$_2$ | O | H | |
| 2.23 | F | Cl | OCH$_2$CH≡CH—Br | O | H | |
| 2.24 | F | Cl | OC$_3$H$_7$-i | O | oxo | |
| 2.25 | F | CN | OC$_3$H$_7$-i | O | H | 162° |
| 2.26 | F | CN | COOC$_4$H$_9$-sec | O | H | |
| 2.27 | F | CH$_3$ | OC$_3$H$_7$-i | O | H | |
| 2.28 | F | Cl | CH$_2$SCH$_3$ | O | H | |
| 2.29 | F | Cl | CH$_2$SO$_2$CH$_3$ | O | H | |
| 2.30 | F | Cl | SO$_2$C$_3$H$_7$-i | O | H | |
| 2.31 | F | Cl | OC$_3$H$_7$-i | O | H | |
| 2.32 | F | Cl | OC$_3$H$_7$-i | O | 8-OH | |
| 2.33 | F | Cl | OC$_3$H$_7$-i | O | 5-CH$_3$ | |
| 2.34 | F | Cl | OC$_3$H$_7$-i | O | 6(7)-CH$_3$ | |
| 2.35 | F | Cl | OC$_3$H$_7$-i | O | 6(7)-C$_2$H$_5$ | |
| 2.36 | F | Cl | OC$_3$H$_7$-i | O | 6(7)-Cl | |
| 2.37 | F | Cl | OC$_3$H$_7$-i | O | 8-F | |
| 2.38 | F | Cl | OC$_3$H$_7$-i | O | 5,8-(CH$_3$)$_2$ | |
| 2.39 | F | Cl | OC$_3$H$_7$-i | O | 5,5,7-(CH$_3$)$_3$ | |
| 2.40 | F | Cl | OCH(CH$_3$)COOCH$_3$ | O | H | |
| 2.41 | F | Cl | OCH(CH$_3$)—CH$_2$CH$_3$ | O | H | |
| 2.42 | F | Cl | OCH$_2$-phenyl | O | H | |
| 2.43 | F | Cl | OCH(CH$_3$)-phenyl | O | H | |
| 2.44 | F | Cl | OC(CH$_3$)H—CH$_2$OCH$_3$ | O | H | |
| 2.45 | F | Cl | OCH$_2$C(O)CH$_3$ | O | H | |
| 2.46 | F | Cl | OCH$_2$CH≡CH$_2$ | O | H | |
| 2.47 | F | Cl | OCH$_2$CH≡CHCl | O | H | |
| 2.48 | F | Cl | OCH$_2$CH(Cl)≡CH$_2$ | O | H | |
| 2.49 | F | Cl | OCH$_2$-(2,2-diCl-cyclopropyl) | O | H | |
| 2.50 | F | Cl | OCH$_2$-(2-Cl-cyclopropyl) | O | H | |
| 2.51 | F | Cl | OCH$_2$-cyclopropyl | O | H | |
| 2.52 | F | Cl | OCH$_2$CH$_2$OCH$_2$CH$_3$ | O | H | |
| 2.53 | F | Cl | OCH$_2$-(2-tetrahydrofuryl) | O | H | |
| 2.54 | F | Cl | OCH$_2$-(2-tetrahydropyranyl) | O | H | |
| 2.55 | F | Cl | OCH$_2$-(2H-5,6-dihydrothiin-3-yl) | O | H | |
| 2.56 | F | Cl | OCH$_2$—C(=NOCH$_3$)—COOC$_2$H$_5$ | O | H | |
| 2.57 | F | Cl | OCH$_2$-(1,3-dioxolan-2-yl) | O | H | |
| 2.58 | F | Cl | OCH$_2$-(1,3-dithiolan-2-yl) | O | H | |
| 2.59 | F | Cl | OCH$_2$-CO-(1,4-oxazin-4-yl) | O | H | |
| 2.60 | F | Cl | OCH$_2$COOC$_5$H$_{11}$-n | O | H | |
| 2.61 | F | Cl | O-(2-oxo-cyclopentyl) | O | H | |
| 2.62 | F | Cl | OP(O)OCH$_3$)$_2$ | O | H | |
| 2.63 | F | Cl | OCH(SCH$_3$)—COOCH$_2$CH$_2$Cl | O | H | |
| 2.64 | F | Cl | OCH$_2$P(O)(OCH$_2$CHd$_3$)$_2$ | O | H | |
| 2.65 | F | Cl | OCH$_2$CF$_3$ | O | H | |
| 2.66 | F | Cl | OCHF$_2$ | O | H | |
| 2.67 | F | Cl | OCH$_2$COO(cyclopentyl) | O | H | |
| 2.68 | F | Cl | OCH$_2$-(1-pyrazolyl) | O | H | |
| 2.69 | F | Cl | 4-[C$_2$H$_3$OOC—CH(CH$_3$)—O]phenoxy | O | H | |
| 2.70 | F | Cl | OCH$_2$-(2-thienyl) | O | H | |
| 2.71 | F | Cl | OCH(CH$_3$)-(3-CH$_3$-1,2,4-oxadiazol-5-yl) | O | H | |
| 2.72 | F | Cl | SC$_3$H$_7$-i | O | H | |
| 2.73 | F | Cl | SCH$_2$C≡CH | O | H | |
| 2.74 | F | Cl | SCH$_2$COOC$_2$H$_5$ | O | H | |
| 2.75 | F | Cl | SCH(CH$_3$)—COOC$_2$H$_5$ | O | H | |
| 2.76 | F | Cl | SCH$_2$-phenyl | O | H | |
| 2.77 | F | Cl | S-(tetrahydro-2-pyranyl) | O | H | |
| 2.78 | F | Cl | NCH$_2$COOC$_2$H$_5$ | O | H | |
| 2.79 | F | Cl | N(CH$_3$)$_2$ | O | H | |
| 2.80 | F | Cl | N—(CH$_3$)COOCH$_2$CH$_3$ | O | H | |
| 2.81 | F | Cl | NHCOCH(CH$_3$)—CH$_2$CH$_3$ | O | H | |
| 2.82 | F | Cl | NHCH(C$_2$H$_5$)—P(O)(C$_2$H$_5$)(OC$_2$H$_5$) | O | H | |
| 2.83 | F | Cl | COOC$_3$H$_7$-i | O | H | 127–128°; 0.28, ethylacetate:hexane 1:1 |
| 2.84 | F | Cl | COOCH(CH$_2$F)$_2$ | O | H | 123–125° |
| 2.85 | F | Cl | COOCH$_2$CH$_2$OCH$_3$ | O | H | |
| 2.86 | F | Cl | COON=C(CH$_3$)$_2$ | O | H | |
| 2.87 | F | Cl | COOCH$_2$CH$_2$F | O | H | 135–136° |
| 2.88 | F | Cl | COOCH$_2$CH$_2$OSi(CH$_3$)$_3$ | O | H | |
| 2.89 | F | Cl | COOCH$_2$Si(CH$_3$)$_3$ | O | H | |
| 2.90 | F | Cl | COOCH$_2$CH$_2$P(O)(OCH$_3$)$_2$ | O | H | |
| 2.91 | F | Cl | COOCH(CH$_3$)CH$_2$Si(CH$_3$)$_3$ | O | H | |
| 2.92 | F | Cl | COOCH(C$_2$H$_5$)P(O)(OCH$_3$)$_2$ | O | H | |
| 2.93 | F | Cl | COOCH$_2$COOC$_2$H$_5$ | O | H | |
| 2.94 | F | Cl | COOCH$_2$OCOCH$_3$ | O | H | |
| 2.95 | F | Cl | COOCH(CH$_3$)OCO-piperidin-1-yl | O | H | |
| 2.96 | F | Cl | CON(CH$_3$)$_2$ | O | H | |
| 2.97 | F | Cl | CON(CH$_3$)(OCH$_3$) | O | H | |
| 2.98 | F | Cl | CONHSO$_2$CH$_3$ | O | H | |
| 2.99 | F | Cl | CONHOCH$_2$COOC$_2$H$_5$ | O | H | |
| 2.100 | F | Cl | CONHCH$_2$COOC$_2$H$_5$ | O | H | |
| 2.101 | F | Cl | CHO | O | H | |
| 2.102 | F | Cl | COCH$_3$ | O | H | |

TABLE 2-continued

| Ex. | | | | $X_1 = X_2$ | $(R_5)_m$ | m.p. or Rf on silical gel |
|---|---|---|---|---|---|---|
| 2.103 | F | Cl | 4-COOC$_2$H$_5$-1,3-dioxolan-2-yl | O | H | |
| 2.104 | F | Cl | 2-CH$_3$-1,3-dioxolan-2-yl | O | H | |
| 2.105 | F | Cl | 4,4-di(CH$_3$)-4,5-di-hydro-1,3-oxazol-2-yl | O | H | |
| 2.106 | F | Cl | CH$_3$ | O | H | |
| 2.107 | F | Cl | CH$_2$CH(CH$_3$)$_2$ | O | H | |
| 2.108 | F | Cl | CH$_2$COOC$_2$H$_5$ | O | H | |
| 2.109 | F | Cl | CH$_2$C(CN)(CH$_3$)COOC$_2$H$_5$ | O | H | |
| 2.110 | F | Cl | CH$_2$C(CH$_3$)(COOC$_2$H$_5$)$_2$ | O | H | |
| 2.111 | F | Cl | CH$_2$OCH$_3$ | O | H | |
| 2.112 | F | Cl | CH$_2$OCH$_2$COOC$_2$H$_5$ | O | H | |
| 2.113 | F | Cl | CH$_2$NHCH$_2$COOC$_2$H$_5$ | O | H | |
| 2.114 | F | Cl | CH$_2$CH$_2$CN | O | H | |
| 2.115 | F | Cl | CH$_2$CH$_2$COOC$_2$H$_5$ | O | H | |
| 2.116 | F | Cl | CH$_2$CH(CH$_3$)—COOC$_2$H$_5$ | O | H | |
| 2.117 | F | Cl | CH=CH—CN | O | H | |
| 2.118 | F | Cl | CH=CH—COOC$_2$H$_5$ | O | H | |
| 2.119 | F | Cl | CH=C(Br)—COOC$_2$H$_5$ | O | H | |
| 2.156 | F | Cl | COOC(CH$_3$)$_3$ | O | H | 0.19, ethylacetate-hexane (1:1) |
| 2.157 | F | Cl | COOCH$_2$CH$_2$CN | O | H | 108–110° |
| 2.158 | F | Cl | OCH(CH$_3$)C≡C—C(CH$_3$)$_3$ | O | H | 0.24, ethylacetate-hexane (1:1) |
| 2.159 | F | Cl | OC(CH$_3$)$_2$C≡CH | O | H | 133–134° |
| 2.160 | F | Cl | CONHC(CH$_3$)$_2$CH$_2$Cl | O | H | 142° |

Compounds of the formula I wherein A and R$_6$ join together to form —N(CX$_2$) so oriented such that N is tied to the C(X$_1$) moiety of formula I, and the moiety 2-R$_2$-4-R$_3$-5-R$_4$-phenyl is represented below as Ar.
Part B:

| Ex. | Ar | $X_1 = X_2$ | $(R_5)_m$ | m.p. or Rf on silical gel |
|---|---|---|---|---|
| 2.120 | 5-F-indan-1-on-6-yl | O | H | |
| 2.121 | 4-(C$_2$H$_5$OOC—CH$_2$)-7-F—AR$_1$ | O | H | |
| 2.122 | 4-(CH$_3$OCH$_2$)-7-F—Ar$_1$ | O | H | |
| 2.123 | 4-(CNCH$_2$)-7-F—Ar$_1$ | O | H | |
| 2.124 | 4-CH$_3$-7-F—Ar$_1$ | O | H | |
| 2.125 | 4-allyl-7-F—Ar$_1$ | O | H | |
| 2.126 | 4-CH$_2$-(tetrahydropyran-4-yl)-7-F—Ar$_1$ | O | H | |
| 2.127 | 4-CH$_2$-(5,6-dihydro-2-H-thiin-3-yl) | O | H | |
| 2.128 | 4-CH$_2$-(2-pyridyl)-7-F—Ar$_1$ | O | H | |
| 2.129 | 4-(pyrazin-2-yl-methyl)-7-F—Ar$_1$ | O | H | |
| 2.130 | 2,25-tri-F-benzo[d]-dioxole-6-yl | O | H | |
| 2.131 | 4-CH$_3$-7-F-benzo[e]-1,3-dioxine-6-yl | O | H | |
| 2.132 | 4-(2-propynyl(-7-F-benzo[b]01,4-thiazin-3-on-6-yl | O | H | |
| 2.133 | 4-(2-propynyl)-7-F—Ar$_1$ | O | H | 212–214° |
| 2.134 | 1-(2-propynyl)-6-F—Ar$_2$ | O | H | |
| 2.135 | 1-allyl-6-F—Ar$_2$ | O | H | |
| 2.136 | 1-(2-propynyl)-6-F—Ar$_3$ | O | H | |
| 2.137 | 1-allyl-6-F—Ar$_3$ | O | H | |
| 2.138 | 1-allyl-6-F-quinoline-2(1H)-on-7-yl | O | H | |
| 2.139 | 3-(2-propynyl)-6-F-benzo[d]-1,3-oxazole-2(3H)-on-5-yl | O | H | |
| 2.140 | 4-(1,2-oxazole-3-yl-CH$_2$)-7-F—Ar$_1$ | O | H | |
| 2.141 | 4-(5-CH$_3$-1,2,4-oxadiazol-3-yl-CH$_3$)-7-F—Ar$_1$ | O | H | |
| 2.142 | 3-(1,2-oxazole-3-yl-CH$_2$)-6-F—Ar$_4$ | O | H | |
| 2.143 | 3-(2-pyridyl-CH$_2$)-6-F—Ar$_4$ | O | H | |
| 2.144 | 5-5F-2,3-dihydro-benzo[b]furan-6-yl | O | H | |
| 2.145 | 5-F-1-CH$_3$-indol-6-yl | O | H | |
| 2.146 | 1-(2-propynyl)-5-F-benzo[d]pyrazol-6-yl | O | H | |
| 2.147 | 1-(2-propynyl)-5-F-benzo[d]-1,2,3-triazol-6-yl | O | H | |
| 2.148 | 1-allyl-5-F-1,3-dihydro-indol-2-on-6-yl | O | H | |
| 2.149 | 5-F-1,3-dimethyl-1,3-dinhydro-indol-2-on-6-yl | O | H | |
| 2.150 | 5-F-benzo[d]imidazol-2(1H,3H)-on-6yl | O | H | |
| 2.151 | 5-F-1-(2-propynyl-1H-indol-2,3-dion-6-yl | O | H | |
| 2.152 | 6-F-chroman-7-yl | O | H | |
| 2.153 | 6-F-2,3-dihydrobenzo[b]-1,4-dioxin-7-yl | O | H | |
| 2.154 | 6-F-1-(2-propynyl)-3,4-dihydroquinolin-2(1H)-on-7-yl | O | H | |
| 2.155 | 7-F-4-isopropyl-chromen-2-on-6-yl | O | H | |

Key to Abreviations
(1) isomeric mixture of 4- and 5-substituted compound
(2) Ar = 2-R$_2$-4-R$_3$-5-R$_4$-phenyl
(3) Ar$_1$ = 2,4-dihydro-benzo[b]-1,4-oxazin-3-on-7yl
(4) Ar$_2$ = 3,4-dihydro-2H-quinoxalin-2-on-7yl
(5) Ar$_3$ = 1 H-quinoxalin-2-on-7-yl
(6) Ar$_4$ = Benzo[d]-1,3-thiazol-2(3H)-on-5-yl
(7) numbering convention

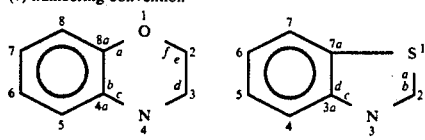

INTERMEDIATE COMPOUNDS

EXAMPLE 3

2-chloro-4-fluoro-5-(4,5,8,8a-tetrahydro-1,3-dioxoimidazo[1,5a]-pyridine-2(3H)-yl)-benzoic acid-1-methylethylester To the stirred solution of 1.9 g (0,0135 mol) of 1,2,3,6-tetrahydro-2-pyridinecarboxylic acid-methyl ester in 50 ml of dry toluene, which contains 1.2 ml of triethylamine, are added without cooling 3.47 g (0.0135 mol) of 2-chloro-4-fluoro-5-isocyanato-benzoic acid-1-methylethylester in 100 ml of dry toluene.

When all the isocyanate has been introduced the resulting reaction solution is stirred at room temperature for a period of 18 hours and is then evaporated in vacuo. The remaining viscous liquid is homogenous by TLC (Rf=0.38 on silica gel, with ethyl acetate-hexane 1:1) and can be used for the preparation of the final product without further purification.

EXAMPLE 4

4,5-Epoxy-2-piperidinecarboxylic acid-methyl ester

To 2,8 g (0.02 mol) of 1,2,3,6-tetrahydro-2-pyridinecarboxylic acid-methyl ester in 20 ml of dry methylene chloride ($CH_2Cl_2$) is added dropwise, without cooling, the dried ($Na_2SO_4$) solution of 4.3 g of m-chloroperbenzoic acid (80%; 0.02 mol) in 100 ml of dry $CH_2Cl_2$. After the exothermic (35°) reaction has subsided, the reaction solution is allowed to cool to ambient and is kept at that temperature in darkness for 6 days. The reaction mixture is then treated with 140 ml of water which contains 14 g of KKH $CO_3$ and 1,5 g of $NaHSO_3$.

The organic layer is separated and washed with 100 ml water.

The residue left on rotevaporation of the dried ($Na_2SO_4$) methylene chloride is subjected to column chromatography on silica gel. Elution with diethyl ether furnishes the title compound, which, upon trituration with diethyl ether, has a m.p. of 104°-106°.

Biology

The herbicidal activity of the compounds of this application is demonstrated by experiments carried out for the pre-emergence and post-emergence control of a variety of weeds. Such weeds include *Abutilon theophrasti, Amaranthus retroflux, Sinapis alba, Solanum nigrum, Bromus tectorum, Setaria viridis, Avena fatua*, and *Echinochloa crus-galli.*

In pre-emergence testing, small plastic greenhouse pots filled with dry soil are seeded with the various weed seeds. Twenty-four hours or less after the seeding, the pots are sprayed with water until the soil is wet and the test compounds formulated as aqueous emulsions of acetone solutions containing emulsifiers are sprayed at the indicated concentrations emulsifiers are sprayed on the surface of the soil. After spraying, the soil containers are placed in the greenhouse and provided with supplementary heat as required and daily or more frequent watering. The plants are maintained under these conditions for a period of from 14 to 21 days, at which time the conditions of the plants and the degree of injury to the plants is rated.

In post-emergence testing, the compounds to be tested are formulated as aqueous emulsions and sprayed on the foliage of the various weed species that have attained a prescribed size. After spraying, the plants are placed in a greenhouse and watered daily or more frequently. Water is not applied to the foliage of the treated plants. The severity of the injury is determined 21 days after treatment and is rated.

In general, the compounds of this application demonstrate good activity against most of the weed varieties noted above. They are particularly active against *Abutilon theophrasti, Amaranthus retroflexus* and *Solanum nigrum*, in both pre- and post-emergence testing.

What is claimed is:

1. A compound of the formula (I)

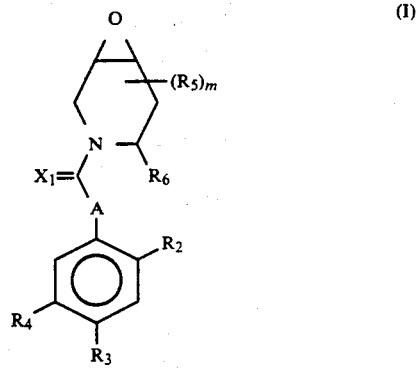

wherein
$R_2$ is halo or hydrogen;
$R_3$ is halo, cyano or $C_{1-4}$alkyl;
$R_4$ is H; halo; $NO_2$; $NH_2$; CN; $C_{1-8}$alkyl optionally substituted by CN; $C_{2-8}$alkenyl optionally substituted by CN; $C_{2-5}$alkinyl; $C_{2-5}$alkoxycarbonyl$C_{1-4}$alkyl, whereby the carbon atom of the alkyl group alpha to the alkoxycarbonyl group may be substituted with one more $C_{2-5}$alkoxycarbonyl groups or a cyano group; $C_{2-5}$alkoxycarbonyl$C_{1-4}$alkoxy$C_{1-4}$alkyl; $C_{2-5}$alkoxycarbonyl$C_{2-5}$alkenyl, whereby the alkenyl group is optionally substituted by halogen; $C_{1-4}$alkylthio$C_{1-4}$alkyl; $C_{1-4}$alkylsulfonyl$C_{1-4}$alkyl; $C_{1-4}$alkylsulfonyl; $C_{1-4}$alkylsulfonyloxy; $C_{1-4}$alkoxy$C_{1-4}$alkoxy; $O(C_{1-4}$alkylene$)_nR_7$; $S(C_{1-4}$alkylene$)_nR_7$; $OCH(SR_8)COOR_9$; $NR_{10}R_{11}$; $COOR_{12}$; $C(O)NR_{13}R_{13}'$; $C(O)R_{14}$; or $R_{15}$;
or $R_3$ and $R_4$ join together with the phenyl ring to form a bicyclic ring containing nine to ten ring atoms, one to three of said ring atoms optionally being selected from oxygen, nitrogen and sulfur, and optionally being substituted with one or more groups selected from $C_{2-8}$alkinyl, halo, oxo, $C_{1-4}$alkylene-$R_{16}$, and $C_{2-8}$alkenyl and $C_{1-8}$alkyl which is itself optionally substituted by $C_{2-5}$alkoxycarbonyl, $C_{1-4}$alkoxy or CN;
$R_5$ is H, $C_{1-4}$alkyl; halogen; OH; $C_{2-4}$alkenyl; or oxo;
$R_6$ is COOH, COOW, COSW, COON=CWW'; $CONHSO_2W$; $CONHOCH_2COOW$; $COOCH_2O-COW$; $COOCHWOCOW'$; or $CONHOCH_2COOH$;
A is NH;
or A and $R_6$ join together to form —N—C($X_2$)— so oriented such that N is tied to the C($X_1$) moiety of formula (I);
$R_7$ is H; $C_{1-4}$alkyl, $C_{2-5}$alkenyl, $C_{2-5}$alkinyl, or $C_{3-8}$cycloalkyl, which hydrocarbyl is unsubstituted or substituted by one or more halo or by CN; cyclopentanonyl; phenyl optionally substituted by $O-C_{1-4}$alkylene—$COOR_8$; $C_{2-5}$alkanoyl; $C_{2-5}$alkoxycarbonyl wherein the alkoxy is optionally substituted by $C_{1-4}$alkylthio; $C(O)NR_8R_8'$; $C(=NOR_8)COOR_8'$; $P(O)(OR_8)OR_8'$; $R_{15}$; $C(O)R_{15}$; or cyclopentoxycarbonyl;

$R_8$ and $R_8'$ independently are $C_{1-4}$alkyl;

$R_9$ is $C_{1-4}$alkyl optionally substituted by one or more halo;

$R_{10}$ is H or $C_{1-4}$alkyl;

$R_{11}$ is H; $C_{1-4}$alkyl, optionally substituted by $P(O)(OR_8)R_8'$; $C_{2-5}$alkanoyl; $C_{2-5}$alkoxycarbonyl; or $C_{2-5}$alkoxycarbonyl$C_{1-4}$-alkyl;

$R_{12}$ is N=$C_{2-8}$alkylidene; or $C_{1-4}$alkyl optionally substituted by one or more groups selected from halo, $C_{1-4}$alkoxy, CN, tri($C_{1-4}$alkyl)silyloxy, tri($C_{1-4}$alkyl)silyl, $C_{2-5}$alkoxycarbonyl, $P(O)(OR_8)OR_8'$, $C_{2-5}$alkanoyloxy, and di($C_{1-4}$alkyl)aminocarbonyloxy in which both alkyl groups may be tied together to form a saturated 5 to 6 membered heteroring optionally containing one further heteroatom selected from O, S and N, and in which any further N-heteroatom present may, depending on the hydrogenation degree of the heteroring, bear a hydrogen or a $C_{1-4}$alkyl group;

$R_{13}$ is H or $C_{1-4}$alkyl; and $R_{13}'$ is H, $C_{1-4}$alkyl optionally substituted by halo, $C_{1-4}$alkoxy, phenyl, CHO, $C_{2-5}$alkanoyl, $C_{1-4}$alkylsulfonyl, $C_{2-5}$alkoxycarbonyl$C_{1-4}$alkyl or $C_{2-5}$alkoxycarbonyl$C_{1-4}$alkoxy;

or $R_{13}$ and $R_{13}'$ together form a 4 to 6 membered heteroring optionally containing one or two further heteroatoms selected from O, S and N, whereby, depending on the hydrogenation degree of the heteroring, any further N-heteroatom may bear hydrogen or be substituted by $C_{1-4}$alkyl;

$R_{14}$ is H or $C_{1-4}$alkyl;

$R_{15}$ is a heterocyclic ring having 5 or 6 ring atoms, one to three of said ring atom being selected from oxygen, sulfur and nitrogen, which ring is optionally substituted with one or more groups selected from $C_{1-4}$alkyl and $C_{2-5}$alkoxycarbonyl;

$R_{16}$ is tetrahydropyranyl, 5,6-dihydro-2H-thiinyl, pyridyl, pyrazinyl, oxazolyl, or oxadiazolyl all of which are optionally substituted with $C_{1-4}$alkyl;

W and W' are independently $C_{1-8}$alkyl, $C_{2-8}$alkenyl, $C_{2-8}$alkinyl, or phenyl, each of which is optionally substituted by CN, $C_{1-4}$alkoxy or one or more halo;

$X_1$ and $X_2$ are independently O or S;

n is 0 or 1; and m is 0 or 2.

2. A compound of formula (I) according to claim 1 wherein A and $R_6$ join together to form —N—C($X_2$)—.

3. A compound of formula (I) according to claim 1 or 2 wherein $X_1$ and $X_2$ are oxygen.

4. A compound of formula (I) according to claim 3 wherein $R_2$ is chlorine or fluorine.

5. A compound of formula (I) according to claim 3 wherein $R_3$ is bromine, chlorine, fluorine, methyl or cyano.

6. A compound of formula (I) according to claim 3 wherein $R_4$ is $COOR_{12}$, $OR_7$ or $CONR_{13}R_{13}'$, $R_7$ is $C_{1-4}$alkyl, $C_{2-5}$alkenyl or $C_{2-5}$alkinyl, $R_{12}$ is $C_{1-4}$alkyl optionally substituted by halo or CN, $R_{13}$ is H and $R_{13}'$ is $C_{1-4}$alkyl optionally substituted by halo.

7. A compound of formula (I) according to claim 3 wherein $R_3$ and $R_4$ join together to form a benzoxazinone optionally substituted by $C_{2-8}$alkinyl.

8. A compound of formula (I) according to claim 3 wherein $R_5$ is hydrogen or fluorine.

9. A compound of formula (I) according to claim 3 wherein $R_2$ is chlorine or fluorine, $R_3$ is bromine, chlorine, fluorine, methyl or cyano, $R_4$ is $COOR_{12}$, $OR_7$ or $CONR_{13}R_{13}'$, $R_7$ is $C_{1-4}$alkyl, $C_{2-5}$alkenyl or $C_{2-5}$alkinyl, $R_{12}$ is $C_{1-4}$alkyl optionally substituted by halo or CN, $R_{13}$ is H, $R_{13}'$ is $C_{1-4}$alkyl optionally substituted by halo and $R_5$ is hydrogen or fluorine.

10. A herbicidal composition comprising a compound of formula (I) as defined in claim 1 and an agriculturally acceptable carrier.

* * * * *